(12) United States Patent
Shibata et al.

(10) Patent No.: US 7,640,809 B2
(45) Date of Patent: Jan. 5, 2010

(54) SPOT WELDING INSPECTING APPARATUS

(75) Inventors: Kaoru Shibata, Tochigi (JP); Noriaki Shigematsu, Tochigi (JP); Mitsutaka Igaue, Tochigi (JP); Noriko Kurimoto, Tochigi (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 12/133,708

(22) Filed: Jun. 5, 2008

(65) Prior Publication Data
US 2009/0031812 A1 Feb. 5, 2009

(30) Foreign Application Priority Data
Jul. 31, 2007 (JP) .............................. 2007-199611

(51) Int. Cl.
G01N 9/24 (2006.01)
(52) U.S. Cl. .............................. 73/622; 73/577; 73/587
(58) Field of Classification Search .................. 73/622, 73/573, 577, 587, 598, 600, 618, 623, 37, 73/37.5, 37.8; 219/91.1
See application file for complete search history.

(56) References Cited

U.S. PATENT DOCUMENTS

| 3,554,029 | A | * | 1/1971 | Deininger, Jr. ............... | 73/620 |
| 3,739,628 | A | * | 6/1973 | Saglio ......................... | 73/627 |
| 3,986,391 | A | * | 10/1976 | Vahaviolos ................... | 73/781 |
| 4,083,223 | A | * | 4/1978 | Hashimoto et al. ........... | 374/5 |
| 4,265,119 | A | * | 5/1981 | Dubetz et al. ................ | 73/588 |
| 5,537,875 | A | * | 7/1996 | Viehmann et al. ............ | 73/588 |
| 5,920,014 | A | * | 7/1999 | Waschkies .................... | 73/597 |
| 6,184,487 | B1 | * | 2/2001 | Visscher ..................... | 219/91.1 |
| 6,250,163 | B1 | * | 6/2001 | MacLauchlan et al. ........ | 73/643 |
| 6,515,251 | B1 | * | 2/2003 | Wind .......................... | 219/86.1 |
| 6,640,632 | B1 | * | 11/2003 | Hatanaka et al. ............. | 73/598 |
| 6,948,369 | B2 | * | 9/2005 | Fleming et al. ............... | 73/588 |
| 7,373,822 | B2 | * | 5/2008 | Waschkies et al. ............ | 73/597 |

FOREIGN PATENT DOCUMENTS

| JP | 11104848 A | * | 4/1999 |
| JP | 2005-527374 | | 9/2005 |

* cited by examiner

Primary Examiner—Hezron Williams
Assistant Examiner—Samir M Shah
(74) Attorney, Agent, or Firm—Rankin, Hill & Clark LLP

(57) ABSTRACT

A spot welding inspecting apparatus is provided with: a gun chip; a signal transmitting part; an ultrasonic sensor; an inner cylinder; a through hole; a partitioning cylinder; a first flow path; a second flow path; and a third flow path.

The inner cylinder is inserted to an outer cylinder of spot welding gun and holds the ultrasonic sensor. The through hole is provided on the inner cylinder. The partitioning cylinder surrounds the through hole and is inserted into a gap between the ultrasonic sensor and the outer cylinder. The first flow path is formed between the inner cylinder and the partitioning cylinder by passing the through hole from an inner portion of the inner cylinder. The second flow path is formed at the gun chip to be circulated around a front end of the partitioning cylinder. The third flow path is formed between the outer cylinder and the partitioning cylinder. A cooling agent flows in an order of the first flow path, the second flow path and the third flow path.

4 Claims, 11 Drawing Sheets

SPOT WELDING INSPECTING APPARATUS

BACKGROUND OF THE INVENTION

1. Field of the Invention

The present invention relates to a spot welding inspecting apparatus which is mounted in a spot welding gun and capable of inspecting a welded portion by an ultrasonic sensor.

2. Background Art

In spot welding, a weld metal molten and solidified at a contact portion of, for example, two sheets of steel plates after welding is referred to as a nugget. A bonding strength of a welded portion is evaluated by a nugget diameter indicating a size of the nugget.

In inspecting after welding, as an apparatus of measuring the nugget diameter utilizing a nondestructive inspection method, there is proposed an electrode including an ultrasonic probe at inside thereof (refer to, for example, Patent Reference 1).

[Patent Reference 1] JP-T-2005-527374 (FIG. 1, FIG. 2)

Patent Reference 1 will be explained in reference to the following drawings.

FIG. 15 is a view for explaining a basic constitution of a related art. A welding electrode 100 is constituted by a shaft 102, an ultrasonic probe 106, a probe holder 107, a cooling water pipe 108, and a signal line 109. The shaft 102 has a hollow shape and is attached with a welding cap 101 at a front end thereof. The ultrasonic probe 106 is mounted in the welding cap 101 and a front end portion 105 of the shaft 102 by way of a connection pad 104 placed at an inner bottom portion 103 of the welding cap 101. The probe holder 107 holds the ultrasonic probe 106 from a rear side and is inserted into the shaft 102.

The cooling water pipe 108 extends from the probe holder 107 and is inserted into the shaft 102. The signal line 109 extends from a rear end of the ultrasonic probe 106 to an upper side of the drawing and is inserted into the probe holder 107 and the cooling water pipe 108.

According to the welding electrode 100 of Patent Reference 1, as shown by arrow marks, cooling water flows from a rear end portion 111 of the cooling water pipe 108. The cooling water passes a periphery of the ultrasonic probe 106 by way of an inner portion of the probe holder 107. The cooling water changes a flowing direction at the inner bottom portion of the welding cap 101. Then, the cooling water flows along the periphery of the ultrasonic probe 106 and a partition plate 112 attached to a lower portion of the probe holder 107. Finally, the cooling water flows out from a rear end portion 113 of the shaft 102 in the hollow shape as indicated by arrow marks.

The welding electrode 100 can be cooled by the flow of the cooling water.

The inventors have carried out spot welding by using a welding electrode having a structure of the welding electrode 100 of Patent Reference 1, and tried to inspect a bonding portion immediately thereafter. As a result thereof, the cooling water flowing at an inner portion of the welding electrode 100 flows deviatedly in a constant direction to be along the partition plate 112. Therefore, it has been found that cooling of the welding cap 101 is deviated.

The cooling water at the inner portion of the welding electrode 100 is divided in two to a side (cool water side) in which cooling is positively carried out by passing the cooling water and a side (warm water side) in which the cooling water is not supplied sufficiently and cooling becomes insufficient by receiving heat from the welded portion. Therefore, the ultrasonic probe 106 is dipped to both sides of the cool water side and the warm water side. So, there is a concern of bringing about a deterioration in a measurement accuracy and a reduction in a durability by thermal shock in the ultrasonic probe 106 by heat transmitted from the warm water side.

In addition thereto, in FIG. 2 of Patent Reference 1, according to the welding electrode, a pad 16 and a welding cap 12 are brought into close contact with each other by pressing a probe 14 by a spring element. However, there is a case in which the pad 16 and the welding cap 12 are insufficiently brought into close contact with each other to hamper transmission of an ultrasonic signal.

SUMMARY OF THE INVENTION one or more embodiments of the invention provide a spot welding inspecting apparatus capable of nondeviatedly cooling a gun chip and capable of realizing to stabilize measurement of an ultrasonic sensor and a reduction in thermal shock to the ultrasonic sensor.

Moreover, one or more embodiments of the invention provide a spot welding inspecting apparatus capable of promoting a stability of transmission of an ultrasonic signal.

In accordance with one or more embodiments of the invention, a spot welding inspecting apparatus is provided with: a gun chip fitted to one end of an outer cylinder of a spot welding gun; a signal transmitting part mounted in the gun chip and configured to transmit a signal; an ultrasonic sensor having a cylindrical shape, one end of the ultrasonic sensor being brought into contact with the signal transmitting part; an inner cylinder inserted to the outer cylinder and holding the ultrasonic sensor; a through hole provided on the inner cylinder; a partitioning cylinder surrounding the through hole and inserted into a gap between the ultrasonic sensor and the outer cylinder, a front end of the partitioning cylinder reaching the signal transmitting part; a first flow path formed between the inner cylinder and the partitioning cylinder by passing the through hole from an inner portion of the inner cylinder; a second flow path formed at the gun chip to be circulated around a front end of the partitioning cylinder; and a third flow path formed between the outer cylinder and the partitioning cylinder.

In the spot welding inspecting apparatus, the first, second and third flow paths are configured so that a cooling agent flows in an order of the first flow path, the second flow path and the third flow path.

In the embodiments, the spot welding inspecting apparatus is constituted such that the cooling agent can be made to flow in an order of the first flow path, the second flow path and the third flow path. The first flow path is formed between the inner cylinder and the partitioning cylinder. The second flow path is formed at the gun chip in the cap-like shape to be circulated around a front end of the partitioning cylinder.

The third flow path is formed between the outer cylinder and the partitioning cylinder. As a result, there is not present a large obstacle for disturbing a flow in circumferential directions and longitudinal directions of the first flow path, the second flow path and the third flow path. Therefore, the flow of the cooling agent is not deviated in a constant direction as in Patent Reference 1, and therefore, the gun chip can undeviatedly be cooled.

Further, the ultrasonic sensor is held by the inner cylinder, and the cooling agent is made to flow to the first flow path formed between the inner cylinder and the partitioning cylinder by passing the through hole from the inner portion of the inner cylinder. That is, the ultrasonic sensor provided below the inner cylinder is always brought into contact with the cooling agent flowing through the first flow path, and therefore, the ultrasonic sensor does not undergo a temperature change by warm water as in Patent Reference 1. Therefore, the ultrasonic sensor is stabilized in measurement and is less deteriorated by the thermal shock.

As described above, according to the embodiments, there can be provided the spot welding inspecting apparatus capable of cooling the gun chip undeviatedly and capable of realizing stabilization of measurement by the ultrasonic sensor and a reduction in the thermal shock to the ultrasonic sensor.

According to the embodiments, the second flow path may constituted by a plurality of groove portions formed on an outer peripheral face of the signal transmitting part. Accordingly, the cooling agent is always made to flow to the groove portions, and therefore, the signal transmitting part can sufficiently be cooled. Therefore, thermal deformation of the signal transmitting part in a spot welding operation can be prevented.

In accordance with one or more embodiments of the invention, a spot welding inspecting apparatus is provided with: a gun chip configured to be brought into contact with a work; an ultrasonic sensor mounted in a spot welding gun and configured to transmit an ultrasonic signal to the work; and a signal transmitting part mounted in the gun chip, a front end of the signal transmitting part being brought into contact with the gun chip, and a rear end of the signal transmitting part is being brought into contact with the ultrasonic sensor. The signal transmitting member includes a male screw portion on an outer peripheral face of the signal transmitting member, the gun chip includes a female screw in an inner peripheral face of the gun chip, and the male screw portion is engaged with the female screw portion.

In the embodiments, the signal transmitting part includes the male screw portion to be engaged with the female screw portion provided at the inner peripheral face of the gun chip at the outer peripheral face. A degree of bringing the signal transmitting part and the gun chip into close contact with each other is promoted, and therefore, stability of transmitting the ultrasonic signal can be promoted. Accordingly, there can be provided the spot welding inspecting apparatus capable of promoting stability of transmitting the ultrasonic signal.

In accordance with one or more embodiments of the invention, a spot welding inspecting apparatus is provided with: a shank; a gun chip engaged with a front end of the shank and configured to be brought into contact with a work; an ultrasonic sensor mounted in a spot welding gun and configured to transmit an ultrasonic signal to the work; and a signal transmitting part mounted in the gun chip, a front end of the signal transmitting part being brought into contact with the gun chip, and a rear end of the signal transmitting part being brought into contact with the ultrasonic sensor. A front end of the shank presses the rear end of the signal transmitting part.

In the embodiments, the front end of the shank presses the rear end of the signal transmitting member, and therefore, the signal transmitting part can firmly be held. Accordingly, there can be provided the spot welding inspecting apparatus capable of firmly holding the signal transmitting part.

Other aspects and advantages of the invention will be apparent from the following description, the drawings and the claims.

DETAILED DESCRIPTION OF THE EXEMPLARY EMBODIMENTS

Exemplary embodiments of the invention will be explained as follows in reference to the attached drawings.

Figure 1:
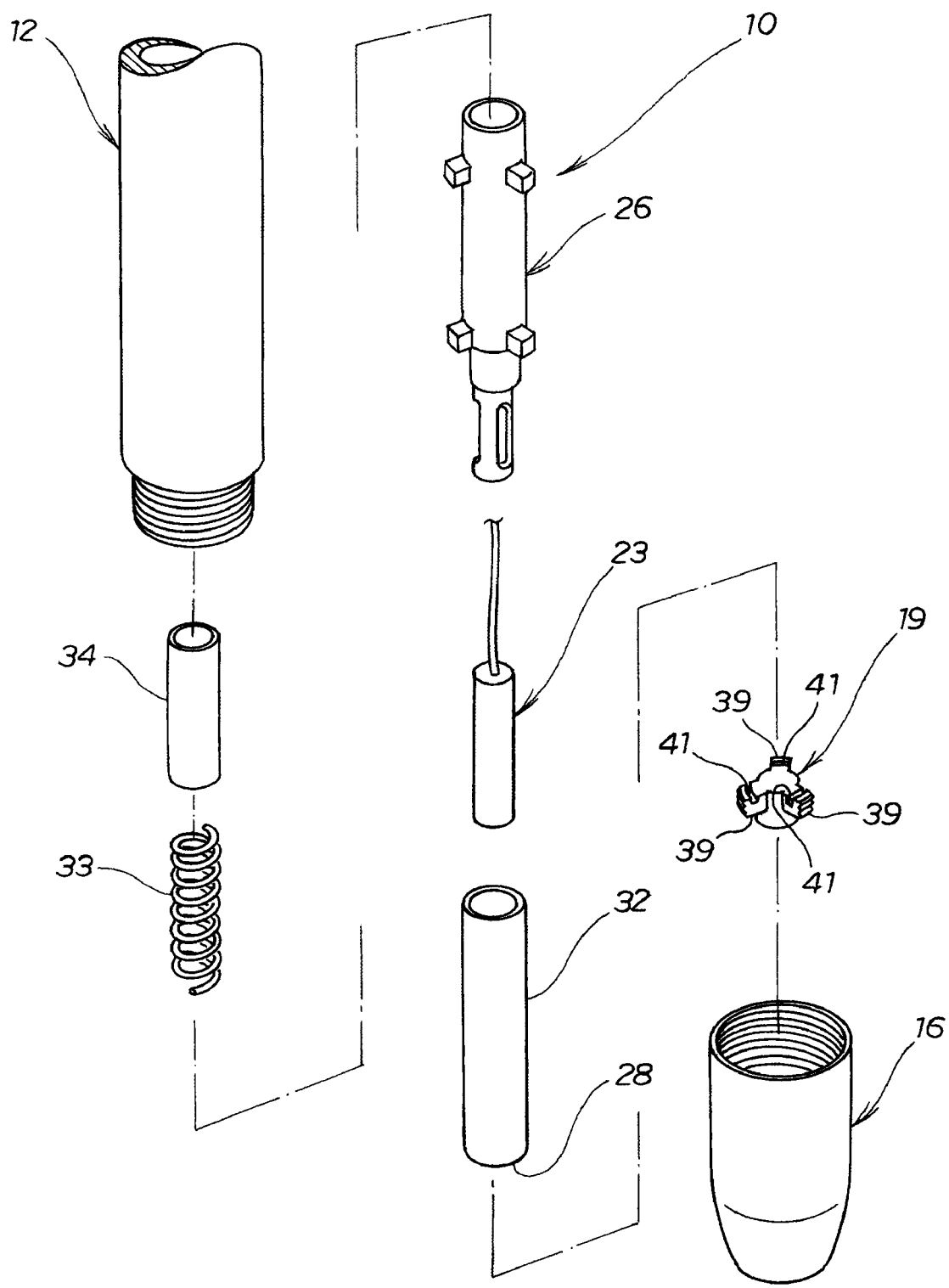
FIG. 1 is a disassembled perspective view of a spot welding inspecting apparatus according to a first exemplary embodiment.

FIG. 1 is a disassembled perspective view of a spot welding inspecting apparatus according to a first exemplary embodiment.

The spot welding inspecting apparatus 10 is an electrode chip of an ultrasonic sensor including type constituted by integrating an outer cylinder 12, a gun chip 16 in a cap-like shape, a signal transmitting part 19, a reflecting type ultrasonic sensor 23 of, for example, a cylindrical shape, an inner cylinder 26, a partitioning cylinder 32, a compression coil spring 33 and a holding cylinder 34.

Figure 2:
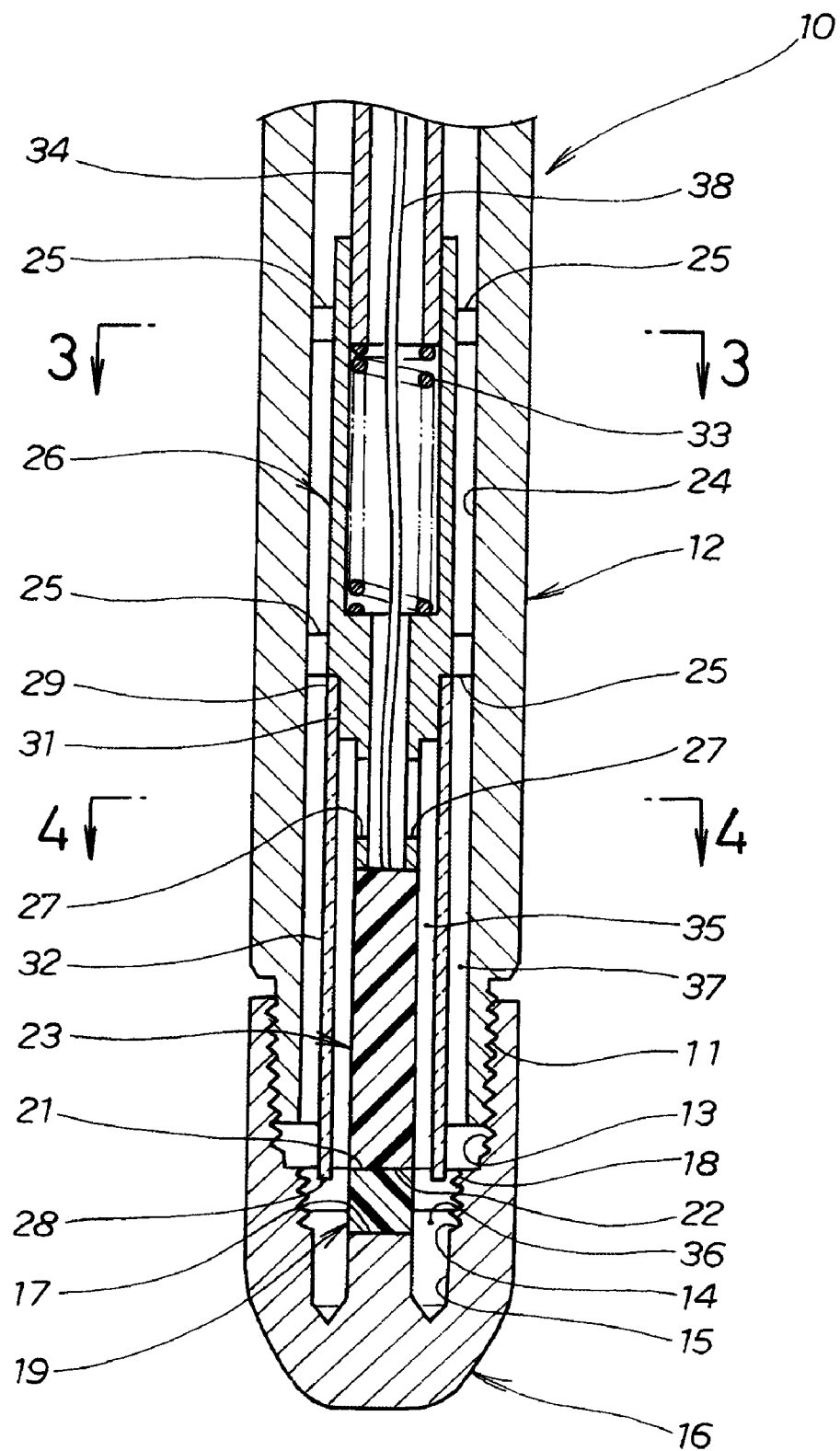
FIG. 2 is a sectional view of the spot welding inspecting apparatus.

FIG. 2 is a sectional view of the spot welding inspecting apparatus of the first exemplary embodiment. The spot welding inspecting apparatus 10 is constituted by the outer cylinder 12 constituting an outlook constituting member of a spot welding gun and including a first male screw portion 11 formed by, for example, a taper screw at an outer face of a front end portion, the gun chip 16 in a cap-like shape including a first female screw portion 13 formed by, for example, a taper screw capable of being screwed to the first male screw portion 11 at an inner face of a rear end portion, including a second female screw portion 14 at a middle portion of the inner face and including a heat conducting groove 15 formed in a lower direction of the drawing from the second female screw portion 14, the signal transmitting part 19 (details of which will be described later) made of a resin mounted to a projected portion 17 provided at a middle portion of the inner face of the gun chip 16 in the cap-like shape and including a second male screw portion 18 capable of being screwed to the second female screw portion 14, the reflection type ultrasonic sensor 23 in the cylindrical shape a front end 22 of which is brought into close contact with a rear end face 21 of the signal transmitting part 19 by way of, for example, an adhering agent, the inner cylinder 26 inserted to the outer cylinder 12 for holding the reflection type ultrasonic sensor 23 having a cylindrical shape and including a plurality of pieces of fixing projections 25 . . . ( . . . designate a plurality of pieces. The same as follows) at a middle portion and a rear end portion to be brought into contact with an inner face 24 of the outer cylinder 12, a plurality of through holes 27 . . . (details of which will be described later) provided at a front end portion of the inner cylinder 26, and the partitioning cylinder 32 made of glass which surrounds the through holes 27 . . . and in which a front end 28 inserted to a gap between the reflection type ultrasonic sensor 23 of the cylindrical shape and the outer cylinder 12 reaches the signal transmitting part 19 and a rear end portion 29 is fitted to a projected portion 31 provided at a front end portion of the inner cylinder 26.

Further, the spot welding inspecting apparatus 10 is constituted to include a first flow path 35 passing the through holes 27 . . . from an inner portion of the inner cylinder 26 and formed between the inner cylinder 26 and the partitioning cylinder 32, a second flow path 36 formed at the gun chip 16 in the cap-like shape to circular around the front end 28 of the partitioning cylinder 32, and a third flow path 37 formed between the outer cylinder 12 and the partitioning cylinder 32 to be able to make the cooling water as, for example, a cooling agent flow in an order of the first flow path 35, the second flow path 36, and the third flow path 37.

Numeral 38 designates a cable extended from the reflection type ultrasonic sensor 23 of the cylindrical shape.

Further, although the first male screw portion 11 and the first female screw portion 13 are formed by the taper screws, the first male screw portion 11 and the first female screw portion 13 may be constituted by parallel screws, and therefore, the first male screw portion 11 and the first female screw portion 13 may be changed to other kinds of screws.

Further, although the adhering agent is used for integrating the signal transmitting part 19 and the reflection type ultrasonic sensor 23 of the cylindrical shape, a contact portion thereof may be constituted to be coupled by a screw, and therefore, the integration may be changed to other coupling method.

Referring back to FIG. 1, the signal transmitting portion 19 includes three pieces of support portions 39 . . . lower portions of which are formed by a cylindrical shape and upper portions of which are trifurcated. Upper faces of three pieces of the support portions 39 . . . are respectively formed with fixing grooves 41, and the fixing screws 41 are fitted with the front end 28 of the partitioning cylinder 32.

Figure 3:
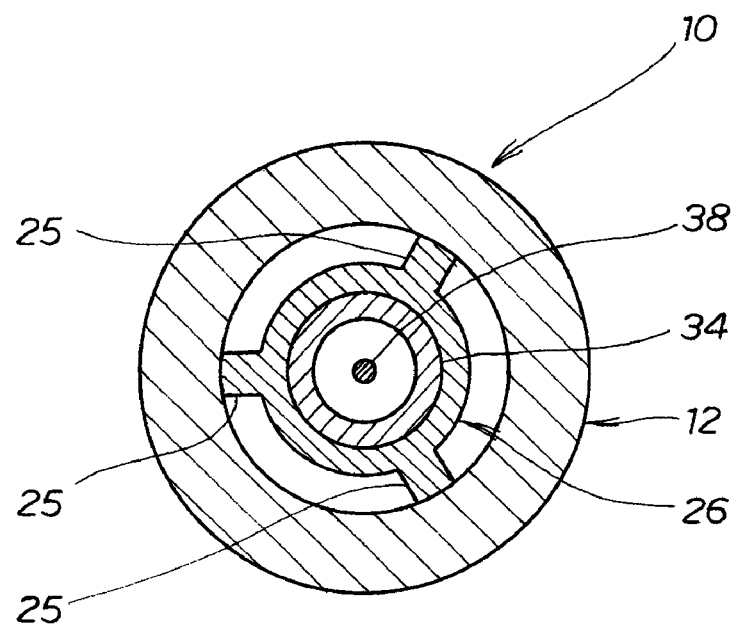
FIG. 3 is a sectional view taken along a line 3-3 of FIG. 2.

FIG. 3 is a sectional view taken along a line 3-3 of FIG. 2.

The inner cylinder 26, the holding cylinder 34 and the cable 38 are inserted to the outer cylinder 12. The inner cylinder 16 includes, for example, 3 piece of fixing projections 25 . . . projected from an outer face of the inner cylinder 26 to an inner face of the outer cylinder 12. Therefore, the reflection type ultrasonic sensor (notation 23 in FIG. 2) in the cylindrical shape can stably be held without being moved in an up and down direction and in a left and right direction of the drawing.

Thereby, a positional shift of the reflection type ultrasonic sensor in the cylindrical shape can be prevented.

Further, although an explanation has been given by constituting a number of pieces of the fixing projections 25 . . . by three pieces, the number of pieces may be changed by outer diameters of the outer cylinder 12 and the inner cylinder 16 and the number of pieces is not limited to three pieces.

Further, referring back to FIG. 2, also with regard to the fixing projections 25 . . . provided at a middle portion of the inner cylinder 26, a similar effect can be achieved.

Figure 4:
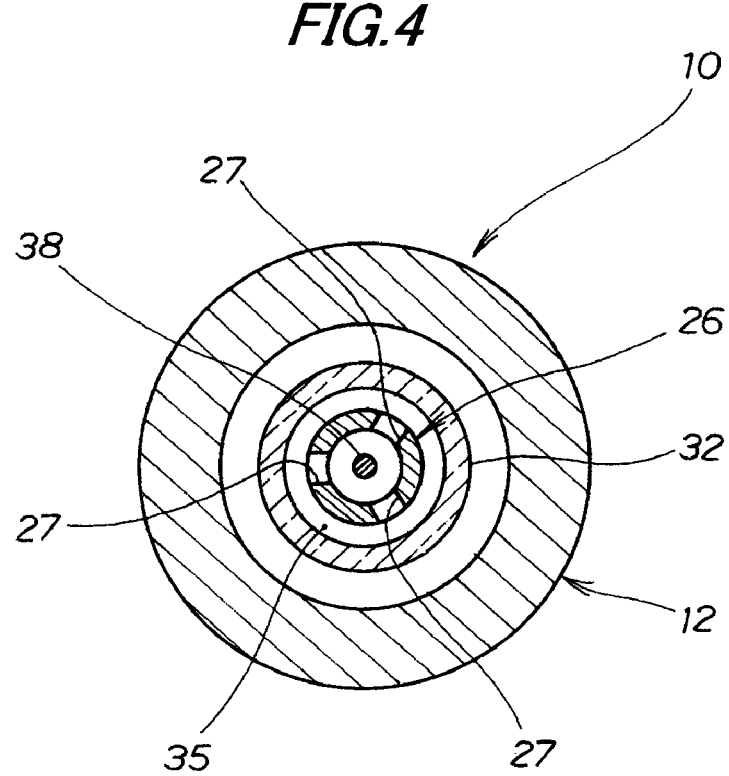
FIG. 4 is a sectional view taken along a line 4-4 of FIG. 2.

FIG. 4 is a sectional view taken along a line 4-4 of FIG. 2.

The partitioning cylinder 32, the inner cylinder 26 and the cable 38 are inserted to the outer cylinder 12. The inner cylinder 26 includes, for example, three pieces of the through holes 27 . . . constituted by penetrating a wall thickness of the inner cylinder 26. Therefore, when the cooling water flows in from a head direction to a tail direction of the drawing of the inner cylinder 26, the cooling water can be made to flow to be dispersed from three pieces of the through holes 27 . . . to the first flow path 35. Thereby, the cooling water can be prevented from flowing deviatedly in a constant direction.

Further, although an explanation has been given by constituting a number of pieces of the through holes 27 . . . by three pieces, the number of pieces may be changed by outer diameters of the inner cylinder 26 and the partitioning cylinder 32 and the number of pieces are not limited to three pieces.

Figure 5:
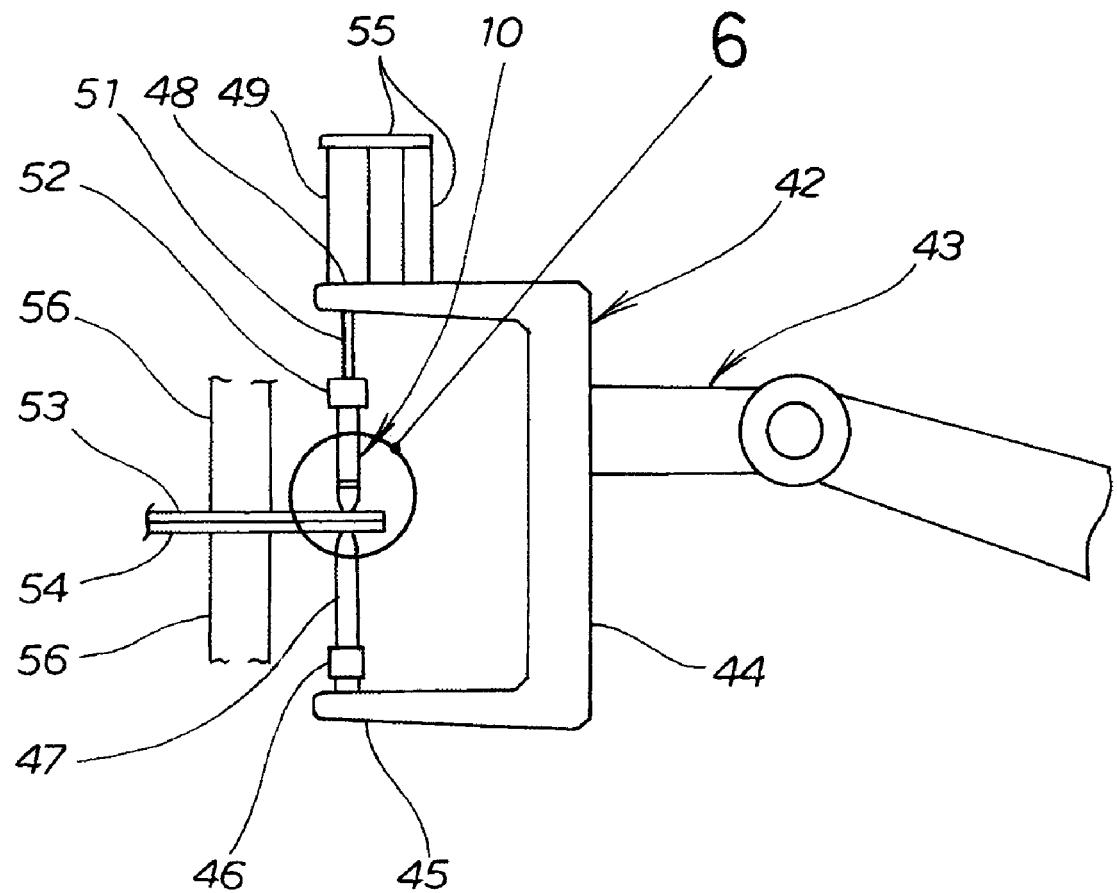
FIG. 5 is an explanatory view of attaching the spot welding inspecting apparatus.

FIG. 5 is an explanatory view of attaching the spot welding inspecting apparatus according to the first exemplary embodiment.

A spot welding gun 42 is constituted by a C type frame 44 attached to a front end of a robot arm 43, a fixing side holder 46 provided to a lower side finger portion 45 of the C type frame 44, a fixing side electrode chip 47 attached to the fixing side holder 46, a cylinder unit 49 provided to an upper side finger portion 48 of the C type frame 44, a movable side holder 52 attached to a cylinder rod 51 of the cylinder unit 49, and the spot welding inspecting apparatus 10 attached to the movable side cylinder 52.

In the drawing, a nugget diameter after welding is measured by the spot welding inspecting apparatus 10 in a state of squeezing two sheets of steel plates 53, 54 laminated by the fixing side electrode chip 47 and the spot welding inspecting apparatus 10.

Numeral 55 designates a support member of the cylinder unit, numerals 56, 56 designate work holders.

An operation of the spot welding inspecting apparatus 10 constituted by the above-described constitution will be explained as follows.

Figure 6:
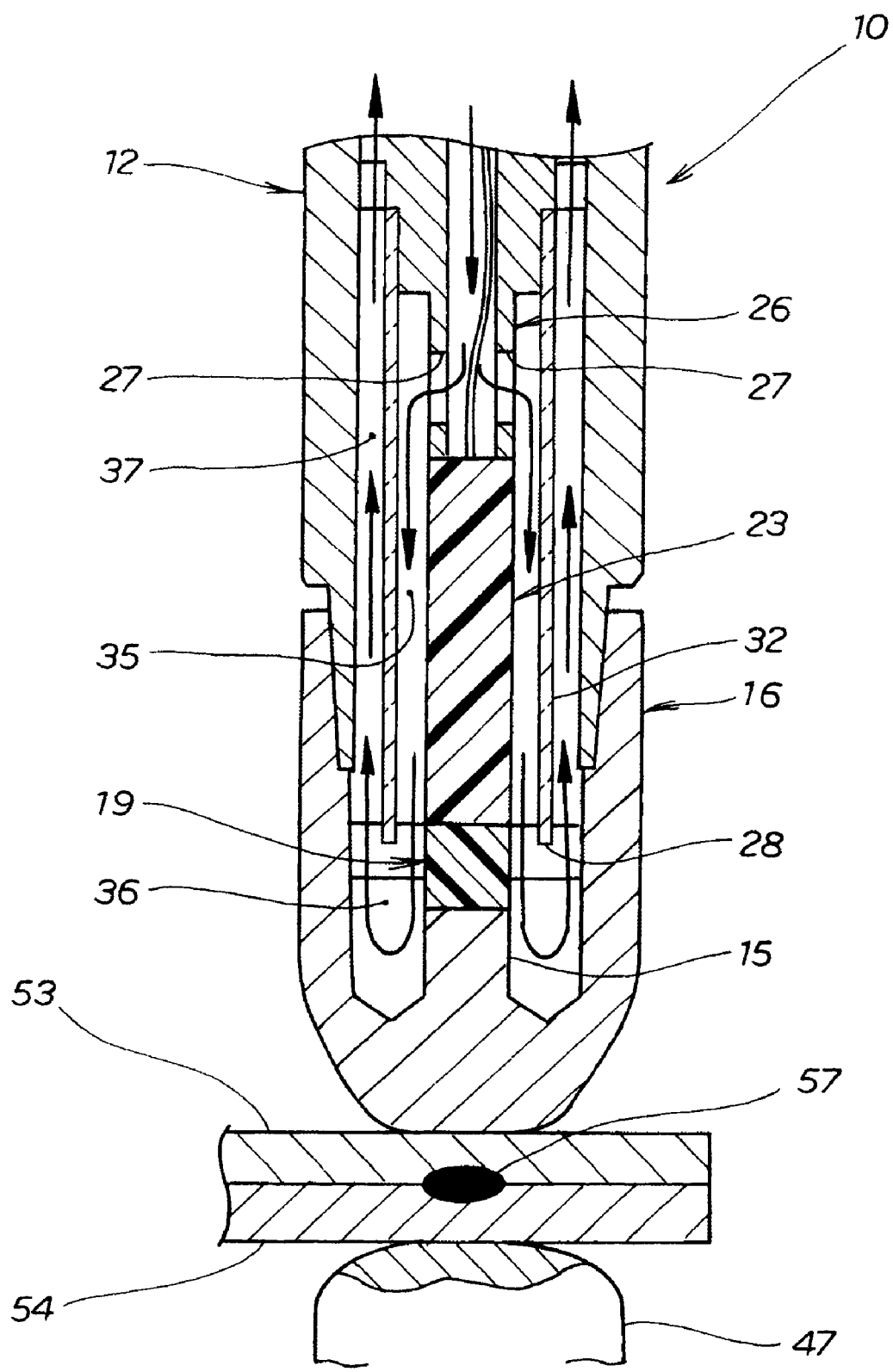
FIG. 6 is a view enlarging portion 6 of FIG. 5.

FIG. 6 is a view enlarging portion 6 of FIG. 5. A nugget 57 is formed at a contact face of the steel plate 53 and the steel plate 54 laminated together after finishing to weld. By continuously supplying cooling water to the inner cylinder 26 as shown by arrow marks, the cooling water flows from the inner portion of the inner cylinder 26, passes the through holes 27 . . . , flows in an order of the first flow path 36, the second flow path 36 and the third flow path 37 and continuously flows out from the outer cylinder 12.

When the nugget diameter is measured under the state, an ultrasonic signal is shot from the reflection type ultrasonic sensor 23 in the cylindrical shape to the nugget 57 by way of the signal transmitting part 19. The ultrasonic signal is reflected by a reflecting face provided at the fixed side electrode chip 47 and a reflecting wave is received by the reflection type ultrasonic sensor 23 in the cylindrical shape.

The nugget diameter can be predicted from information of the provided reflecting wave.

In measuring the nugget diameter, a flow of cooling water is not deviated by the first flow path 35, the second flow path 36 and the third flow path 37, and therefore, the reflection type ultrasonic sensor 23 in the cylindrical shape can always be dipped in the cooling water. Therefore, stable measurement can be realized without bringing about an erroneous operation or the like in measuring.

Further, when the cooling water flows through the second flow path 36, the cooling water passes the heat conducting groove 15. The heat conducting groove 15 is formed in a ring-like shape in view of a section provided by cutting the gun chip 16 in the cap-like shape in head and tail direction of the drawing, and therefore, the flow of the cooling water is not deviated. Further, the heat conducting groove 15 is formed to be dug down deeply to the inner face of the gun chip 16 in the cap-like shape, and therefore, cold by the cooling water is made to be easy to be conducted to the front end portion of the gun chip 16 in the cap-like shape. Thereby, two sheets of the steel plates 53 and 54 can firmly be cooled, and therefore, the cold amounts to stabilize to form the nugget 57.

Therefore, the spot welding inspecting apparatus 10 is constituted to be able to make the cooling water flow in the order of the first flow path 35, the second flow path 36 and the third flow path 37. The first flow path 35 is formed at the gun chip 16 in the cap-like shape to circulate between the inner cylinder 26 and the partitioning cylinder 32, the second flow path 36 is formed to circulate around the front end 28 of the partitioning cylinder 32, the third flow path 37 is formed between the outer cylinder 12 and the partitioning cylinder 32, respectively, and there is not present a large obstacle of disturbing the flow in circumferential directions and longitudinal directions of the first flow path 35, the second flow path 36 and the third flow path 37. The flow of the cooling water is not deviated in a constant direction, and therefore, the gun chip 16 in the cap-like shape can undeviatedly cooled.

Further, the reflection type ultrasonic sensor 23 in the cylindrical shape is held by the inner cylinder 26, and the cooling water is made to flow from the inner portion of the inner cylinder 26 to the first flow path 35 formed between the inner cylinder 26 and the partitioning cylinder 32 by passing the through holes 27 . . . . That is, the cooling water flowing through the first flow path 35 is always brought into contact with the reflection type ultrasonic sensor 23 provided below the inner cylinder 26, and therefore, the reflection type ultrasonic sensor 23 does not undergo a temperature change by warm water. Therefore, the reflection type ultrasonic sensor 23 in the cylindrical shape is stabilized in the measurement and is less deteriorated by thermal shock.

As described above, the gun chip 16 in the cap-like can undeviatedly cooled, and stabilization of measurement by the reflection type ultrasonic sensor 23 in the cylindrical shape and a reduction in thermal shock to the ultrasonic sensor 23 can be realized.

Next, an example of changing a material of the signal transmitting part 19 included in the gun chip 16 in the cap-like shape will be described.

Figure 7:
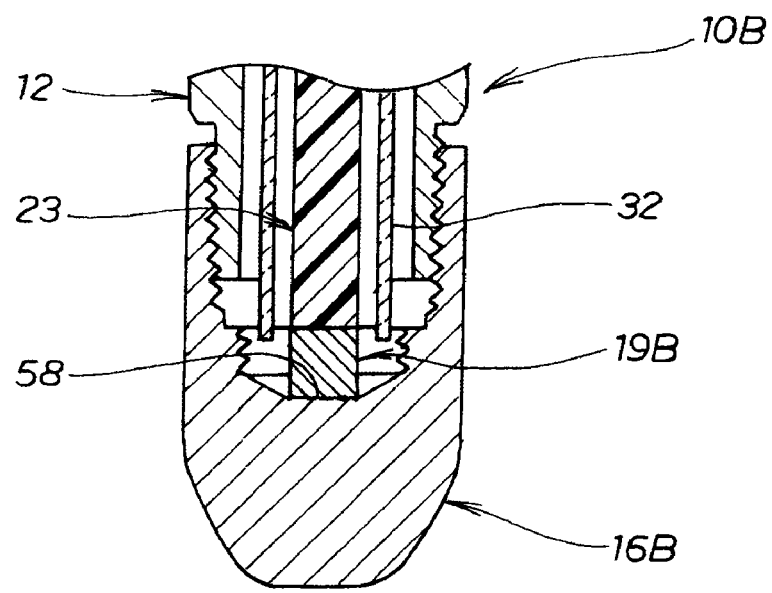
FIG. 7 is a view of a modified example of FIG. 2.

FIG. 7 is a view of an modified example of the first exemplary embodiment. Notations are also used for constitutions common to those of FIG. 2 and an explanation thereof will be omitted.

In a spot welding inspecting apparatus 10B, a flat face 58 is provided at an inner face of a gun chip 16B in a cap-like shape. A signal transmitting part 19B made of copper is mounted to the flat face 58. Since the signal transmitting part 19B is made of copper, cold of the cooling water is facilitated to be transmitted to the gun chip 16B in the cap-like shape.

Further, the gun chip 16B in the cap-like shape does not need to be grooved in contrast to the gun chip 16 in the cap-like shape since the flat face 58 is provided. Therefore, working expense can be reduced, and therefore, the constitution contributes to low price formation of the spot welding inspecting apparatus 10B.

Figure 8:
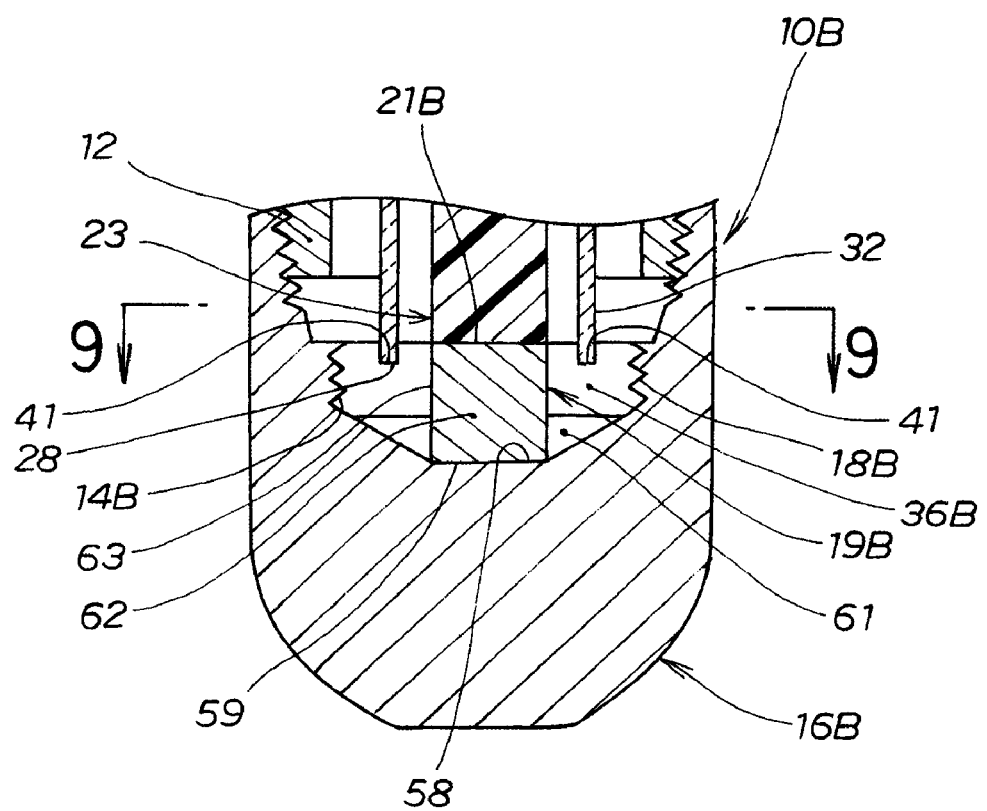
FIG. 8 is a view enlarging a gun chip in a cap-like shape shown in FIG. 7.

FIG. 8 is a view enlarging the gun chip in the cap-like shape shown in FIG. 7, notations are used for constitutions common to those of FIG. 2 and an explanation thereof will be omitted.

The signal transmitting part 19B made of copper is provided with a second male screw portion 18B to be engaged with a screw portion 14B provided at an inner peripheral face of the gun chip 16B in the cap-like shape at an outer peripheral face thereof.

Therefore, a degree of bringing the signal transmitting part 19B and the gun chip 16B into close contact with each other is promoted, and therefore, there can be provided the spot welding inspecting apparatus 16B capable of promoting a stability of transmitting the ultrasonic signal.

Further, the signal transmitting part 10B does not hamper transmission of the ultrasonic signal transmitted from the reflection type ultrasonic sensor 23 in the cylindrical shape since a rear end face 21B is formed in a flat face shape and a front end face 59 is attached to be brought into contact with the flat face 58 of the gun chip 16B in the cap-like shape.

Numeral 61 designates a ring-like flow path provided at an inner bottom portion of the gun chip in the cap-like shape, numeral 62 designates a cylindrical portion of the signal transmitting part, and numeral 63 designates an outer peripheral face of the cylindrical portion.

Figure 9:
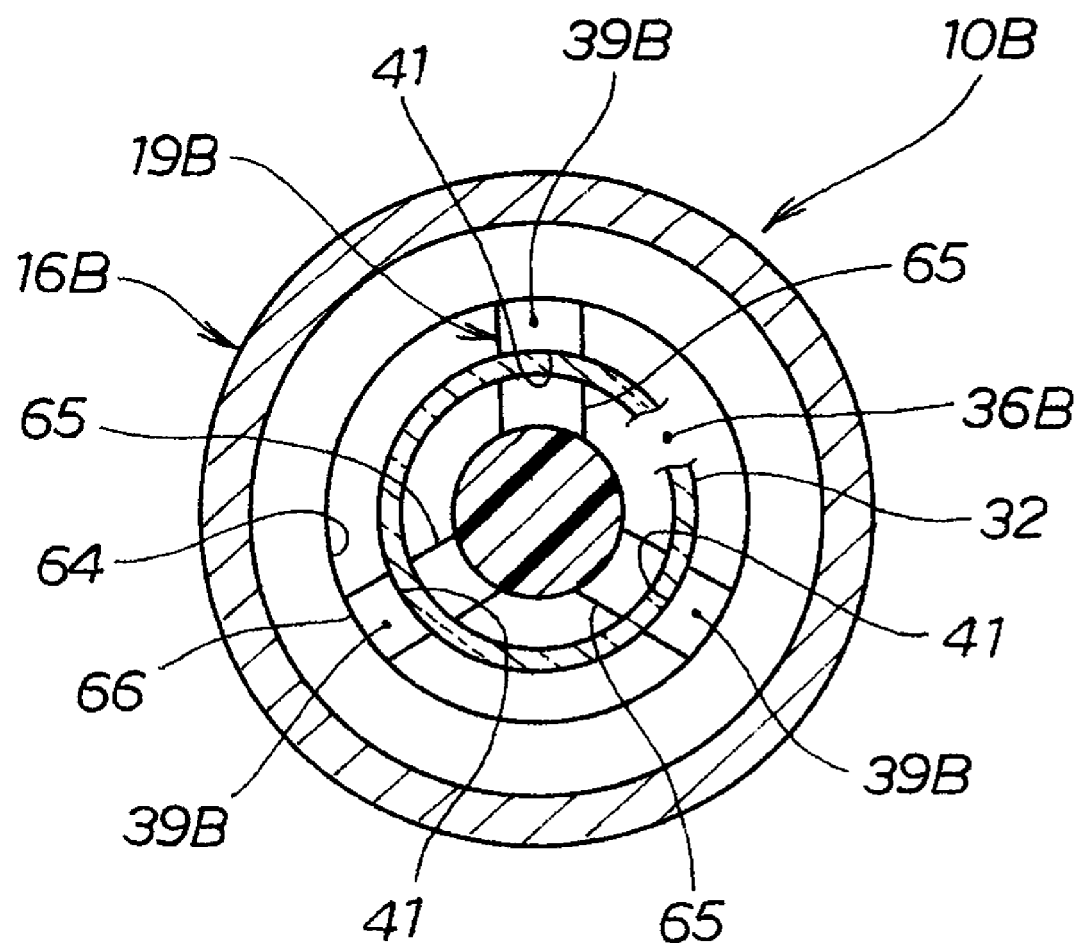
FIG. 9 is a sectional view taken along a line 9-9 of FIG. 8.

FIG. 9 is a sectional view taken along a line 9-9 of FIG. 8, and a second flow path 36B is constituted by an inner peripheral face 64 of the gun chip 16B in the cap-like shape, three pieces of support portions 39B, 39B, 39B projected from the cylindrical portion (notation 62 in FIG. 8) of the signal transmitting part 19B to an outer side in a diameter direction and, for example, three pieces of grooves portions 65, 65, 65 formed at the outer peripheral face (notation 63 in FIG. 8) of the cylindrical portion, and a ring-like flow path (notation 61 in FIG. 8) formed in a tail direction of the drawing of the support portions 39B, 39B, 39B.

That is, the second flow path 36B is constituted by, for example, three pieces of the groove portions 65, 65, 65 notched to be formed at an outer peripheral face 66 of the signal transmitting part 19B by constituting outer peripheral faces of the support portions 39B, 39B, 39B as the outer peripheral face 66 of the signal transmitting part 19B.

Further, although a number of the groove portions 65 is constituted by three pieces in the above-described, the number is arbitrary and the number is not limited to three pieces.

A cooing agent always flows in the groove portions 65, 65, 65, and therefore, the signal transmitting part 19B can sufficiently be cooled. Therefore, thermal deformation of the signal transmitting part 19B can be prevented in a spot welding operation.

Further, the front end (notation 28 in FIG. 8) of the partitioning cylinder 32 is fitted to the fixing grooves 41, 41, 41 of the support portions 39B, 39B, 39B provided at an upper portion of the signal transmitting part 19B, and therefore, the partitioning cylinder 32 can be prevented from being shifted in an up and down direction and in a left and right direction of the drawing when the cooling agent is made to flow.

Although according to the spot welding inspecting apparatus 10 and 10B are explained above, the signal transmitting parts 19 and 19B are coupled to the gun chips 16 and 16B by screws, an explanation will be given as follows of an example in which the signal transmitting part can be fixed to the gun chip without using screw coupling.

Figure 10:
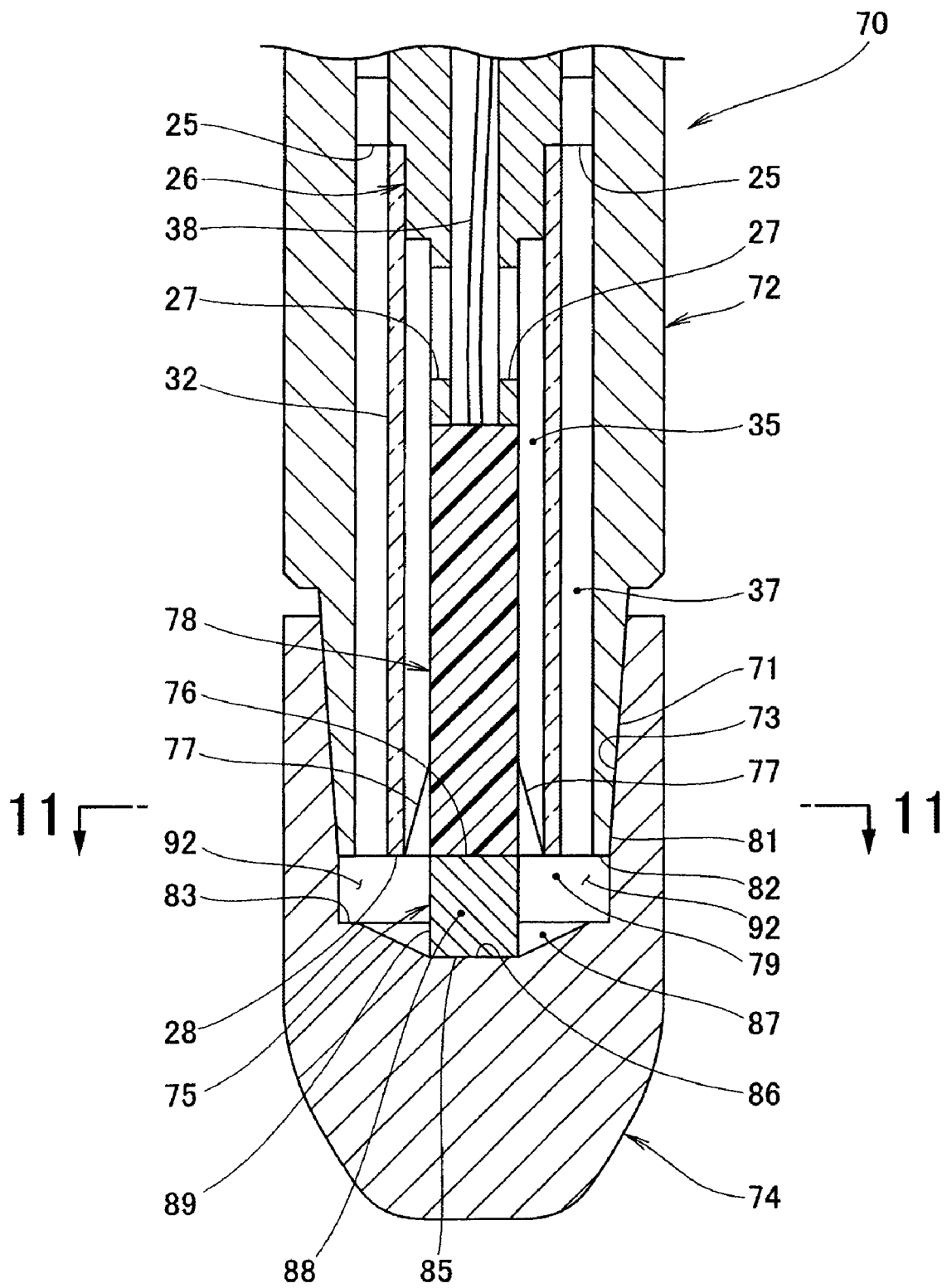
FIG. 10 is a sectional view of a spot welding inspecting apparatus according to a second exemplary embodiment.

FIG. 10 is a sectional view of other spot welding inspecting apparatus according to a second exemplary embodiment. Notations are used for constitutions common to those of FIG. 2 and an explanation thereof will be omitted. Further, in the second exemplary embodiment, an explanation will be given by changing a name of the outer cylinders of the spot welding inspecting apparatus 10 and 10B to shank. A main point of a change resides in that the signal transmitting part is held by a front end of the shank.

A spot welding inspecting apparatus 70 includes a shank 72 in, for example, a shape of a cylinder a front end portion of which is formed by a converging shape to be, for example, a taper portion 71, a gun chip 74 having a cylindrical shape in, for example, a cross-sectional view thereof provided with, for example, a taper portion 73 to constitute an engaging portion formed at an inner periphery to be engaged with the taper portion 71 of the shank 72, a reflection type ultrasonic sensor 78 in, for example, a cylindrical shape provided with a plurality of sheets of projected members 77, (described later in details) transmitting an ultrasonic signal and provided at a lower end portion thereof, a signal transmitting part 75 in, for example, a circular shape which is included in the gun chip 74 and in which a front end face 85 constituting a front end is brought into contact with a flat face 86 provided at an inner bottom portion of the gun chip 74 and a rear end face 76 constituting a rear end is brought into contact with the reflection type ultrasonic sensor 78, and a contact face 82 which includes a second flow path 79 formed at the gun chip 74 to be circulated around the front end 28 of the partitioning cylinder 32 and in which a front end 81 of the taper portion 71 of the shank 72 is brought into contact with the rear end face 76 constituting the rear end of the signal transmitting part 75 and the signal transmitting part 75 is pressed by the contact face 82.

Further, although an explanation has been given of a method of coupling the shank 72 and the gun chip 74 such that the taper portion 73 provided at the gun chip 74 is fitted to the taper portion 71 provided to the shank 72 as described above, the shank 72 and the gun chip can be coupled by screws, and therefore, the method may be changed to other coupling method.

Further, although an explanation has been given such that the shank 72, the gun chip 74, the reflection type ultrasonic sensor 78 and the signal transmitting part 75 are respectively formed by shapes of cylinders and the circular shape, the cylindrical shape, the cylindrical shape in cross-like sectional views thereof, otherwise, the shank 72, the gun chip 74, the reflection type ultrasonic sensor 78 and the signal transmitting part 75 can respectively be formed by shapes of square pipes, a square shape, a square pillar shape, a square shape in cross-sectional views thereof, and therefore, the shapes may be changed to other shapes.

Numeral 83 designates an attaching seat in a circumferential shape, numeral 87 designates a ring-like flow path provided at an inner bottom portion of the gun chip in the cap-like shape, numeral 88 designates a cylindrical portion of the signal transmitting part, and numeral 89 designates an outer peripheral face of the cylindrical portion.

According to the spot welding inspecting apparatus 70, the contact face 82 provided at the front end 81 of the shank 72 is made to press the rear end face 76 constituting the rear end of the signal transmitting part 75, and therefore, the signal transmitting part 75 can firmly be held.

Figure 11:
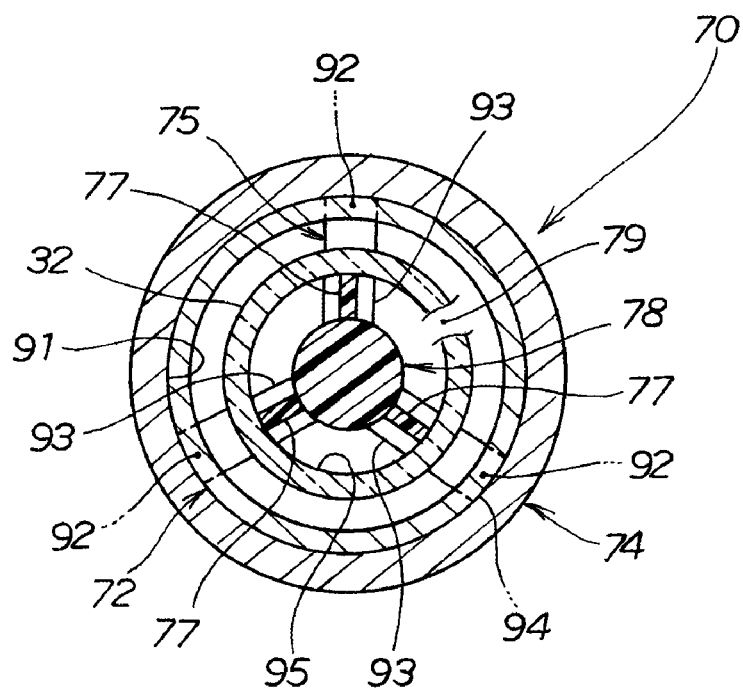
FIG. 11 is a sectional view taken along a line 11-11 of FIG. 10.

FIG. 11 is a sectional view taken along a line 11-11 of FIG. 10, and the second flow path 79 is constituted by an inner peripheral face 91 of the gun chip 74, for example, three pieces of support portions 92, 92, 92 projected from the cylindrical portion (notation 88 in FIG. 10) of the signal transmitting part 75 to an outer side in a diameter direction and, for example, three pieces of groove portions 93, 93, 93 formed by the outer peripheral face (notation 89 in FIG. 10) of the cylindrical portion, and the ring-like flow path (notation 87 in FIG. 10) formed in a tail direction of the drawing of the support portions 92, 92, 92.

That is, the second flow path 79 is constituted by three pieces of groove portions 93, 93, 93 notched to be formed at an outer peripheral face 94 of the signal transmitting part 75 by constituting outer peripheral faces of the support portions 92, 92, 92 as the outer peripheral face 94 of the signal transmitting part 75.

Further, although a number of the support portions 92 is constituted by three pieces as described above, the number is arbitrary, and therefore, the number of the support portions 92 is not limited to three pieces.

Further, although a number of the groove portions 93 is constituted by three pieces as described above, the number is arbitrary, and therefore, the amount of the groove portions 93 is not limited to three pieces.

A cooling agent is always made to flow through the grooves 93, 93, 93, and therefore, the signal transmitting part can sufficiently be cooled.

Further, the reflection type ultrasonic sensor 78 in the cylindrical shape is attached such that, for example, 3 sheets of the projecting members 77, 77, 77 are brought into contact with the inner peripheral face 75 of the partitioning cylinder 32, and therefore, when the cooling agent is made to flow, the partitioning cylinder 32 can be prevented from being shifted in an up and down direction and in a left and right direction of the drawing.

Figure 12:
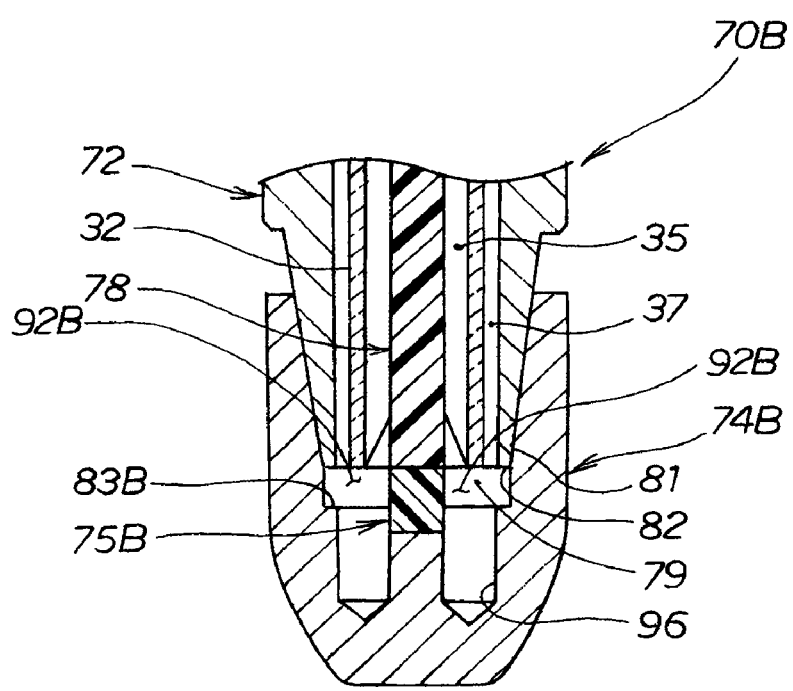
FIG. 12 is a view of a modified example of FIG. 10.

FIG. 12 is a view of a modified example the second exemplary embodiment shown in FIG. 10. Notations are used for constitutions common to those of FIG. 10 and an explanation thereof will be omitted. A point of a major change resides in that the material of the signal transmitting part is changed from copper to resin.

According to a spot welding inspecting apparatus 70B, a gun chip 74B in a circular shape in, for example, cross-sectional view includes an attaching seat 83B in, for example, a circumferential shape at an inner peripheral face, and the attaching seat 83B in the circumferential shape is fitted with a signal transmitting part 75B made of a resin formed in, for example, a circular shape. Notation 92B designates a support portion.

Further, although the shank 72, the gun chip 72B, the attaching seat 83B, the reflection type ultrasonic sensor 78 and the signal transmitting part 75B are respectively formed in shapes of the cylinders and in a circular shape, a circumferential shape, a cylindrical shape, a circular shape in cross-sectional views thereof, otherwise, the shank 72, the gun chip 72B, the attaching seat 83B, the reflection type ultrasonic sensor 78, and the signal transmitting part 75B can respectively be formed by a square shape, a square peripheral shape, a square pillar shape, a square shape, and therefore, the shapes may be changed to other shapes.

The cooling agent is made to flow in an order of the first flow path 35, the second flow path 79, a heat conducting groove 96, and the third flow path 37, and therefore, the cooling agent is always brought into contact with the signal transmitting part 75B. Therefore, the signal transmitting part 75B can be prevented from being deformed by welding heat.

According to the spot welding inspecting apparatus 70 and 70B explained above, the signal transmitting parts 75 and 75B are held by contact faces at front ends of the shanks. When the signal transmitting part and the gun chip are coupled by a screw in addition thereto, the signal transmitting part and the gun chip are further strongly fixed. An explanation will be given as follows of an embodiment in which a signal transmitting part is pressed by a contact face of a front end of a shank and the signal transmitting part and the gun chip are coupled by a screw.

Figure 13:
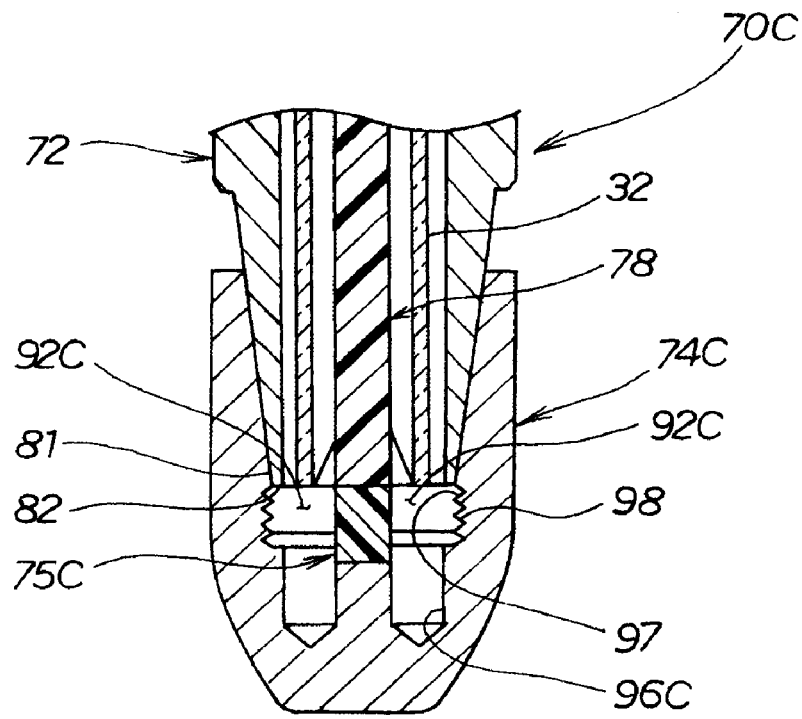
FIG. 13 is a view of a modified example of FIG. 12.

FIG. 13 is a view of a modified example of FIG. 12, notations are used for constitutions common to those of FIG. 12 and an explanation thereof will be omitted. A point of a major change resides in that a method of attaching the signal transmitting part to the gun chip is changed from press-fitting to screw coupling.

According to a spot welding inspecting apparatus 70C, a signal transmitting part 75C is attached to a gun chip 74C by screwing a second male screw portion 98 provided at an outer peripheral face of the signal transmitting part 74C in a circular shape made of a resin to a second female screw portion 97 provided at an inner peripheral face of the gun chip 74C in, for example, a circular shape in a cross-sectional view. Notation 92C designates a support portion and notation 96C designates a heat conducting groove.

Further, although the shank 72, the gun chip 74C and the reflection type ultrasonic sensor 78 are formed respectively by shapes of cylinders, a circular shape, and a cylindrical shape in a cross-sectional view, otherwise, the shank 72, the gun chip 74C and the reflection type ultrasonic sensor 78 can be formed respectively by shapes of square pipes, a square shape and a square pillar shape in cross-sectional views, and therefore, the shapes may be changed to other shapes.

According to the spot welding inspecting apparatus 70C, a degree of bringing the signal transmitting part 75C and the gun chip 74C into close contact with each other is promoted, and therefore, stability of transmitting an ultrasonic signal can be promoted.

Figure 14:
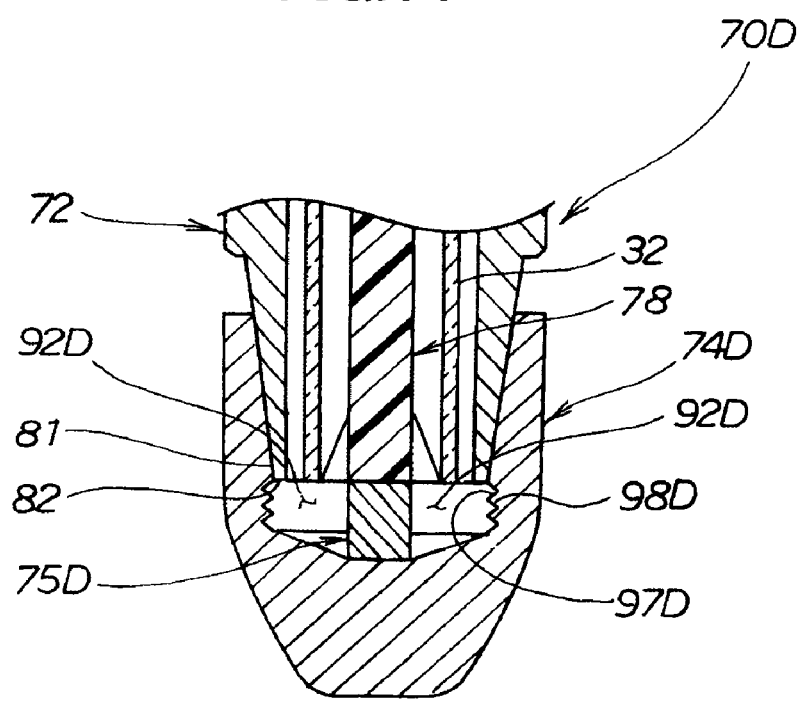
FIG. 14 is a view of a further modified example of FIG. 10.
Figure 15:
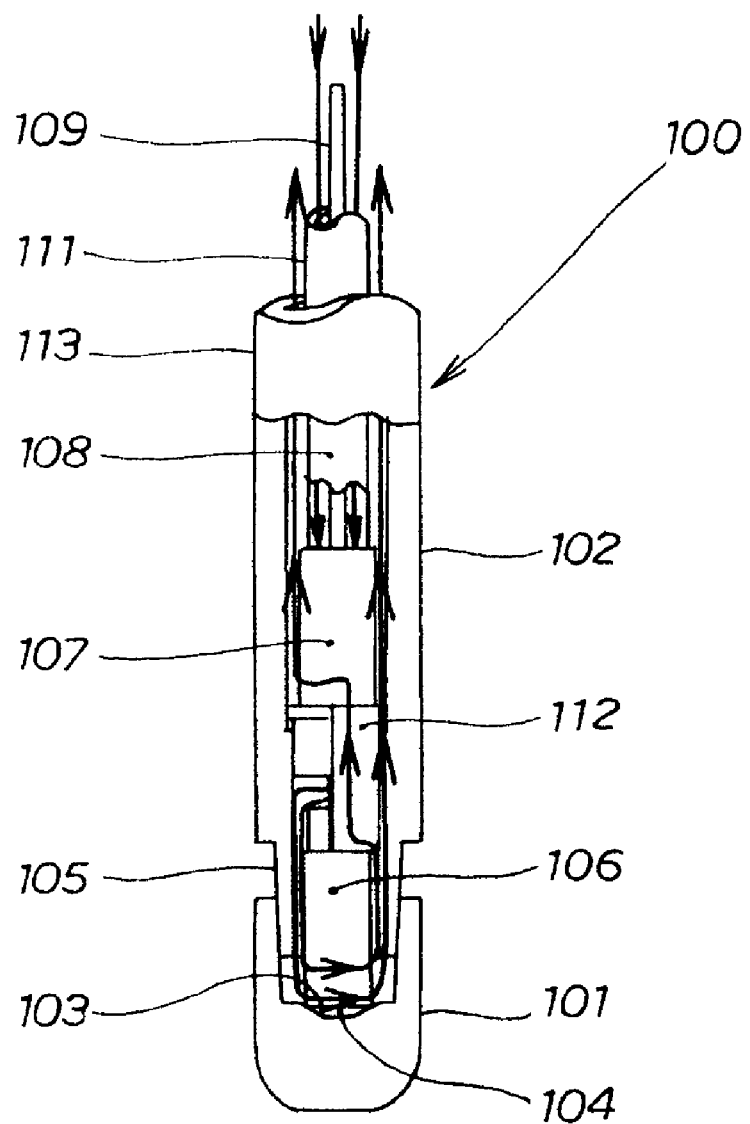
FIG. 15 is a view for explaining a basic constitution of a background art.

FIG. 14 is a view of a further modified example of FIG. 10.

Notations are used for constitutions common to those of FIG. 10 and an explanation thereof will be omitted. A point of a major change resides in that similar to FIG. 13, a method of attaching a signal transmitting part to a gun chip is changed from press-fitting to screw coupling.

According to a spot welding inspecting apparatus 70D, a signal transmitting part 75D is attached to a gun chip 74D by screwing a second male screw portion 98D provided at an outer peripheral face of the signal transmitting part 75D made of copper and in a circular cylinder shape to a second female screw portion 97D provided at an inner peripheral face of the gun chip 74D in, for example, a circular shape in a cross-sectional view. Notation 92D designates a support portion.

Further, although the shank 72, the gun chip 74D and the reflection type ultrasonic sensor 78 are respectively formed by shapes of cylinders and a circular shape and a cylindrical shape in a cross-sectional view, otherwise, the shank 72, the gun chip 72D, and the reflection type ultrasonic sensor 78 can respectively be formed by a square shape and a square pillar shape in cross-sectional views, and therefore, the shapes may be changed to other shapes.

According to the spot welding inspecting apparatus 70D, a degree of bringing the signal transmitting part 75D and the gun chip 74D into close contact with each other is promoted, and therefore, stability of transmitting an ultrasonic signal can be promoted.

Further, although an explanation has been given of the ultrasonic sensor used in the spot welding inspecting apparatus of the invention by the reflection type in the embodiment, a transmission type can be adopted, and therefore, the ultrasonic sensor may be changed to other type.

Further, although the cooling water is adopted in the embodiment for the cooling agent used in the spot welding inspecting apparatus of the invention, an incombustible gas or liquid is applicable, and therefore, other cooling medium may be applied.

Further, although an explanation has been given such that a method of coupling an outer cylinder and a gun chip in a cap-like is constituted by screw coupling in the embodiment, for example, the outer cylinder and the gun chip in the cap-like shape can be coupled by fitting, for example, a projected member provided in an axial direction at an outer face of the outer cylinder and a groove portion provided in the axial direction at an inner face of the gun chip in the cap-like shape, and therefore, the method may be changed to other coupling method.

Further, although an explanation has been given such that a signal transmitting part is coupled to a gun chip in a cap-like shape by a screw in the embodiment, it can be adopted to press-fit a signal transmitting part which is not screwed to the gun chip in the cap-like shape, and therefore, the method may be changed to other coupling method.

While description has been made in connection with specific exemplary embodiments and modified examples of the present invention, it will be obvious to those skilled in the art that various changes and modification may be made therein without departing from the present invention. It is aimed, therefore, to cover in the appended claims all such changes and modifications falling within the true spirit and scope of the present invention.

The spot welding inspecting apparatus of the invention is preferably used in a vehicle body fabricating line of an automobile which carries out welding and inspection at high speed.

DESCRIPTION OF REFERENCE NUMERALS AND SIGNS 10, 10B, 70, 70B, 70C, 70D . . . spot welding inspecting apparatus, 12 . . . outer cylinder, 14, 14B, 97, 97B . . . second female screw portions (female screw portions), 16, 16B . . . gun chips in cap-like shape, 18, 18B, 98, 98B . . . second male screw portions (male screw portions), 19, 19B, 75, 75B, 75C, 75D . . . signal transmitting parts, 23 . . . reflection type ultrasonic sensor in cylindrical shape (ultrasonic sensor in cylindrical shape), 26 . . . inner cylinder, 27 . . . through hole, 28 . . . front end of partitioning cylinder, 32 . . . partitioning cylinder, 35 . . . first flow path, 36, 36B, 79 . . . second flow paths, 37 . . . third flow path, 39, 39B, 92, 92B, 92C, 92D . . . support portions, 42 . . . spot welding gun, 57 . . . nugget (welded portion), 58, 86 . . . flat faces, 59, 85 . . . front end faces of signal transmitting parts, 64, 91 . . . inner peripheral faces of gun chips, 65, 93 . . . groove portions, 66, 94 . . . outer peripheral faces of signal transmitting parts, 71 . . . taper portion, 72 . . . shank in cylinder shape (shank), 73 . . . taper portion, 74, 74B, 74C, 74D . . . gun chips in circular shape (gun chips), 76 . . . rear end face of signal transmitting part (rear end of signal transmitting part), 78 . . . reflection type ultrasonic sensor in cylindrical shape (ultrasonic sensor), 81 . . . front end portion of taper portion of shank (front end of shank), 82 . . . contact face, 83, 83B . . . attaching seats in circumferential shape

What is claimed is:

1. A spot welding inspecting apparatus comprising:
   a gun chip fitted to one end of an outer cylinder of a spot welding gun;
   a signal transmitting part mounted in the gun chip and configured to transmit a signal;
   an ultrasonic sensor having a cylindrical shape, one end of the ultrasonic sensor being brought into contact with the signal transmitting part;
   an inner cylinder inserted to the outer cylinder and holding the ultrasonic sensor;
   a through hole provided on the inner cylinder;
   a partitioning cylinder surrounding the through hole and inserted into a gap between the ultrasonic sensor and the outer cylinder, a front end of the partitioning cylinder reaching the signal transmitting part;

a first flow path formed between the inner cylinder and the partitioning cylinder by passing the through hole from an inner portion of the inner cylinder;

a second flow path formed at the gun chip to be circulated around a front end of the partitioning cylinder; and a third flow path formed between the outer cylinder and the partitioning cylinder, wherein the first, second and third flow paths are configured so that a cooling agent flows in an order of the first flow path, the second flow path and the third flow path.

2. The spot welding inspecting apparatus according to claim 1, wherein the second flow path comprises a plurality of groove portions formed on an outer peripheral face of the signal transmitting part.

3. A spot welding inspecting apparatus comprising:

a gun chip configured to be brought into contact with a work;

an ultrasonic sensor mounted in a spot welding gun and configured to transmit an ultrasonic signal to the work; and a signal transmitting part mounted in the gun chip, a front end of the signal transmitting part being brought into contact with the gun chip, and a rear end of the signal transmitting part is being brought into contact with the ultrasonic sensor, wherein the signal transmitting member includes a male screw portion on an outer peripheral face of the signal transmitting member, the gun chip includes a female screw in an inner peripheral face of the gun chip, and the male screw portion is engaged with the female screw portion.

4. A spot welding inspecting apparatus comprising:

a shank;

a gun chip engaged with a front end of the shank and configured to be brought into contact with a work;

an ultrasonic sensor mounted in a spot welding gun and configured to transmit an ultrasonic signal to the work; and a signal transmitting part mounted in the gun chip, a front end of the signal transmitting part being brought into contact with the gun chip, and a rear end of the signal transmitting part being brought into contact with the ultrasonic sensor, wherein a front end of the shank presses the rear end of the signal transmitting part.

* * * * *